United States Patent [19]
Ahmad

[11] Patent Number: 6,117,292
[45] Date of Patent: Sep. 12, 2000

[54] SENSOR PACKAGING HAVING AN INTEGRAL ELECTRODE PLUG MEMBER

[75] Inventor: Farid Ahmad, Collegeville, Pa.

[73] Assignee: Honeywell International Inc, Morristown, N.J.

[21] Appl. No.: 09/074,304

[22] Filed: May 6, 1998

[51] Int. Cl.[7] .................................................. G01N 27/26
[52] U.S. Cl. ........................ 204/416; 422/82.03
[58] Field of Search .................................... 204/416, 403, 204/286; 422/82.03

[56] References Cited

U.S. PATENT DOCUMENTS

| | | |
|---|---|---|
| 4,449,011 | 5/1984 | Kratochvil et al . |
| 5,068,205 | 11/1991 | Baxter et al. . |
| 5,184,107 | 2/1993 | Maurer . |
| 5,833,824 | 11/1998 | Benton ..................................... 204/416 |

FOREIGN PATENT DOCUMENTS

| | | |
|---|---|---|
| 0 116 117 | 8/1984 | European Pat. Off. . |
| 0 307 973 | 3/1989 | European Pat. Off. . |
| 0 467 479 | 1/1992 | European Pat. Off. . |
| 297 04 357 | 9/1997 | Germany . |

OTHER PUBLICATIONS

PCT, International Search Report, European Patent Office, Sep. 8, 1999, PCT/US99/09500.

*Primary Examiner*—T. Tung
*Assistant Examiner*—Alexander S Noguerola
*Attorney, Agent, or Firm*—Anthony Miologos

[57] ABSTRACT

A chemical sensor apparatus and method of making same is disclosed in which an ion sensitive silicon die is sandwiched between an elastomeric media seal and a conductive elastomeric pad contained within a housing. The conductive elastomeric pad contacts a printed circuit board (PCB) which leads from the housing. The die, elastomers and PCB are secured by a press-fit electrically conductive plug, which contacts and makes an electrical connection with the PCB. The plug functions as a counter electrode for the apparatus as well as a mechanical lock that seals the principal components of the apparatus within the housing in a substantially flush hermetic seal.

11 Claims, 6 Drawing Sheets

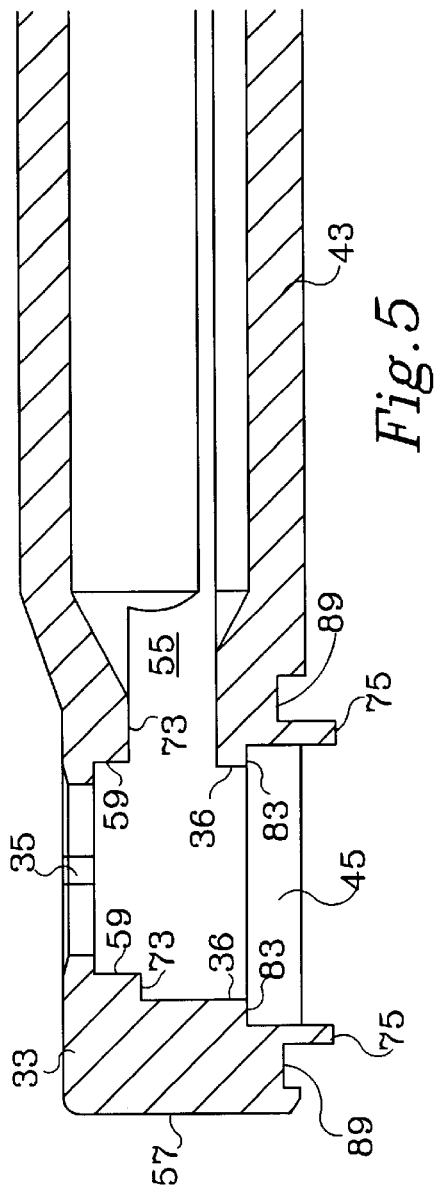
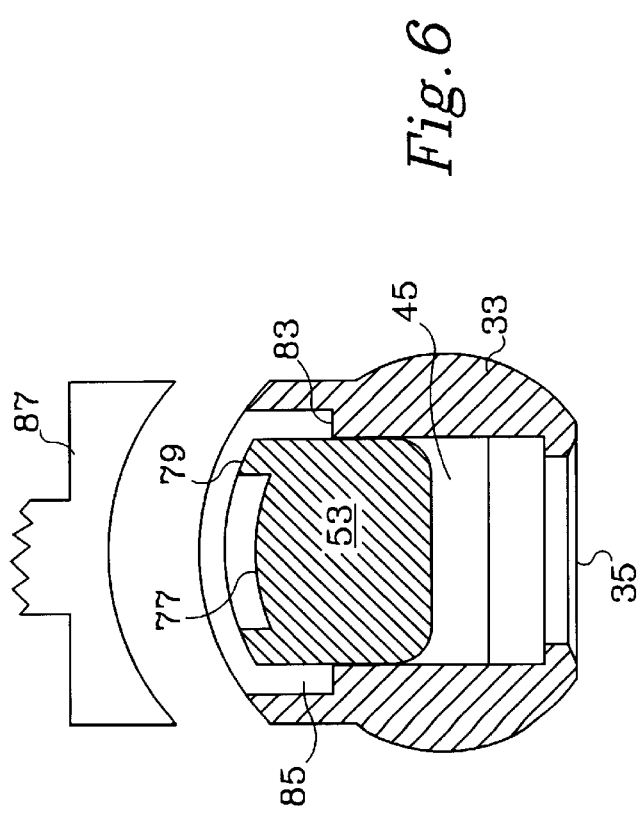

SENSOR PACKAGING HAVING AN INTEGRAL ELECTRODE PLUG MEMBER

BACKGROUND OF THE INVENTION

1. Field of the Invention

This invention relates generally to a method and apparatus for packaging sensors and more particularly to chemical sensors, such as pH sensors, where a microelectronic substrate, such as an ion sensitive field effect transistor (ISFET), is integrally packaged with a counter electrode.

2. Discussion of the Related Art

Various ion sensitive field effect transistors (ISFETs), or microelectronic ion sensors, are known in the art. Such ISFETs have advantages for use as pH sensors such as being solid state, small size and relatively inexpensive to produce.

While semiconductor technology affords the opportunity of fabricating small sensors, reduced physical size introduces significant packaging challenges. An ISFET die includes multiple conductors, which may be routed to external electronic components. Traditional semiconductor packaging design employs electrical contact structures, such as wire bonds, that are made on the same side of the die as the chemical sensing ISFET. Because the sensing ISFET is wetted by the measurement sample, it is critically important to isolate these ISFET electrical contacts from the test liquid sample, particularly when ISFET sensors are operated over a broad range of temperatures and pressures. A first step in obtaining package integrity is to locate contact regions on the ISFET die backside as taught by Baxter in U.S. Pat. No. 4,505,799. While this is an important first step, silicon possesses uniquely different chemical and physical properties, such as a low value of thermal expansion coefficient in comparison with encapsulation polymer materials, which renders it difficult to develop and maintain isolation to process sample over sensor lifetime.

Additional techniques to enhance integrity, in the immediate vicinity of the ISFET die, are described in U.S. Pat. No. 5,068,205. In this known technique, shown in FIG. 1A, a glass header 12 has been utilized wherein the silicon die (ISFET) 17 is adhered to a first side 14 of a borosilicate glass carrier 16 over a through-hole 15 therein. The carrier 16 has a through-hole 15 in it to maintain uncovered the contact areas of the ISFET 17. The carrier 16 also has leads, collectively 18, on the second side 20 thereof to provide electrical access to the ISFET area from the edges of the carrier. The ISFET substrate 17 is electrostatically bonded to the glass carrier 14. Lead wires, collectively 22, are then bonded between the ISFET and the glass carrier leads. The glass carrier leads 18 and back of the ISFET 17 are then covered with an insulating cover 24 for protection. As shown in FIG. 1B, this header assembly 12 is then connected to a flexible circuit 26 for leading out through the probe body 28. This header 12 and circuit 26 assembly are then enclosed within the probe body 28 along with a "J"-shaped Hastelloy counter electrode 27, as detailed in U.S. Pat. No. 4,851,104, and potted with a thermoset polymer to isolate the internal components from the typically corrosive liquids of the sensing environment.

Certain other problems arise in utilizing the ISFET as a practical solution for low-cost sensing applications. Among these is the encapsulation of the device in a body or housing suitable for utilizing the ISFET as part of an ion-sensitive probe for commercial purposes. Typically, the ISFET illustrated in FIG. 1A is potted in a thermoset polymer so that the sensor electronics are not subjected to the often severe environment of the liquid being tested. Effective thermoset polymer encapsulation involves sophisticated assembly processes to obviate voids and to prevent coating of the active ISFET surface. These processes are constrained by the working life of the uncured thermoset polymer. On completion of the filling operation, thermoset polymers typically require additional time for the material to cure.

These aforementioned ISFET sensors are particularly useful when employed in potentiometric electrochemical measurement systems as probes in making pH measurements in industrial environments. In many instances earth-grounded solutions are subject to noise pickup due primarily to parasitic leakage currents flowing from the grounded solution through the measuring electrodes, the associated instrument or analyzer and through the analyzer power supply to the instrument ground. In cases where AC and DC voltages exist between the solution and instrument grounds, currents can be expected to flow via the lowest impedance pathway. This path usually involves unwanted current flow through the measurement liquid sample and the electrodes' lowest impedance path, which typically is the reference electrode. These problems are specially egregious in measurement samples of high purity water of 25° conductivity values of 10 $\mu$Siemens/cm or less. These spurious currents offset or shift the pH reading and cause drift in the sensor output with a commensurate drift in the measurement system accuracy. In order to offset and minimize these spurious currents and their undesirable effects, an additional electrically conductive electrode, or counter electrode, is inserted into the solution being measured in order to channel the spurious currents through this lower impedance electrode rather than through the reference electrode. The counter electrode is usually constructed of a electrically conductive material that is connected to the measurement system electronics and serves the function of the metallized gate in a metal oxide field-effect transistor (MOSFET); namely, it is the primary electrode to enable FET drain voltage and/or drain current control. A better understanding of the counter electrode's function within a potentiometric electrochemical measurement systems may be had by reference to U.S. Pat. No. 4,851,104 to Connery et al.

While the counter electrode technology offers sensor performance benefits, the use of a metallic or alloy material for the counter electrode would provide a location of possible liquid intrusion into the sensor, causing electrical leakage between internal electrode conductors, resulting in sensor malfunction. This intrusion is primarily due to the significantly different physical properties between the counter electrode and the housing and the dissimilar thermal expansion coefficients between these materials.

Design techniques to achieve sensor package integrity entail employing layered levels of protection to provide isolation of sensor conductors and sample fluid. These include backside contact, an electrostatically bonded intermediate structure followed by potting into a sensor subassembly. While this design technique provides for package integrity, it is complex, resulting in assembly costs which are in direct proportion to design and processing complexity.

Hence, there is need for an ion-sensitive microelectronic sensor package which is easily and inexpensively contained in an impervious housing while permitting media access to the ISFET sensor by effectively sealing the probe electronics from the media environment. Additionally, there is a need for packaging techniques that integrate a counter electrode in the sensor housing while eliminating the drawbacks of thermoset encapsulation.

Certain techniques for encapsulating piezoresistive pressure transducers with a conductive elastomeric seal are detailed in U.S. Pat. No. 5,184,107 to Maurer. This patent details a low cost piezoresistive pressure transducer utilizing pre-molded elastomeric seals in which at least one seal is electrically conductive. A piezoresistive, stress-sensitive element in the form of a diaphragm of semiconductor material having a thickened rim is held at its rim between a pair of pre-molded elastomeric seals in a two-piece housing. Electrical connections with external circuitry are made by conductive paths through one of the elastomeric seals, which makes contact with electrical leads that pass through the housing wall.

BRIEF SUMMARY OF THE INVENTION

Therefore, there is provided by the present invention a chemical sensor apparatus and method of making same that is easily and inexpensively manufactured. An ion-sensitive microelectronic substrate, or die, is manufactured which has an ion-sensitive first surface and patterned electrical leads on its second surface. The die is placed between two elastomeric seals, a first media seal, and a second conductive seal. This "sandwich" is then loaded, or placed under pressure, within a media-impervious housing having a media through-hole therein. A PCB (printed circuit board) containing patterned electrical leads communicates electrically with the die through the selectively conductive second elastomeric seal. The first media seal through-hole communicates with the housing media through-hole, thereby exposing the ion-sensitive surface of the ISFET while protecting the other components of the sensor. A plug constructed of an electrically conductive plastic material is then used to mechanically load the PCB, the elastomeric seals and the ISFET in position within the probe housing. The plug also makes an electrical connection to the PCB during mechanical loading and forms an integral counter electrode for the sensor apparatus. The plug is arranged to make a mechanical closure with the housing in such a fashion as to form a substantially flush outer wall with the housing and to press the media seal into a position permitting media access to the ISFET sensor and a hermetic seal of the sensor apparatus electronics from the media environment, thereby eliminating the need for thermoset polymer potting.

By simplifying the ion sensitive pH sensor design and integrating the counter electrode component as part of the sealing mechanism of the apparatus, great advantages are attained in reliability while substantially lowering the overall cost of the probe.

BRIEF DESCRIPTION OF SEVERAL VIEWS OF THE DRAWINGS

The features and advantages of the present invention will be apparent from the following description of a preferred embodiment thereof, taken in conjunction with the sheets of drawings, in which:

FIG. 5 is a cross-sectional of the sensor probe before having the internal components installed.

FIGS. 6 and 7 are a cross-sectional view and a top-perspective view of the plug member and housing of the present invention, respectively.

DETAILED DESCRIPTION OF THE INVENTION

Figure 1A:
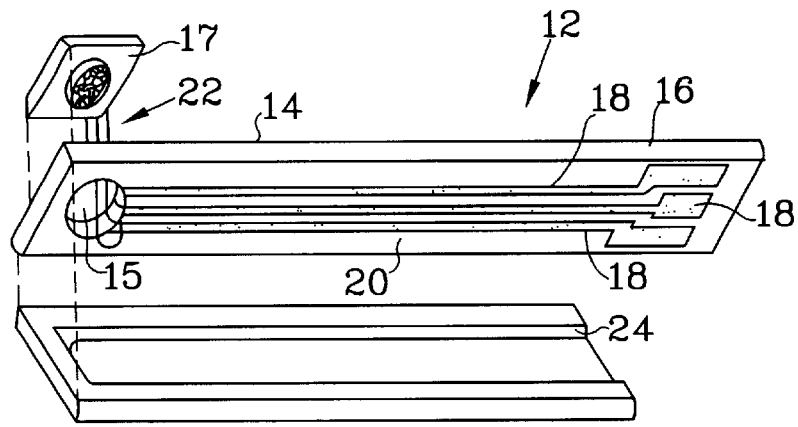
FIGS. 1A and 1B are representations of a known ISFET sensor.

Throughout the Description of the Preferred Embodiment, like components will be identified by like reference numerals.

Figure 2:
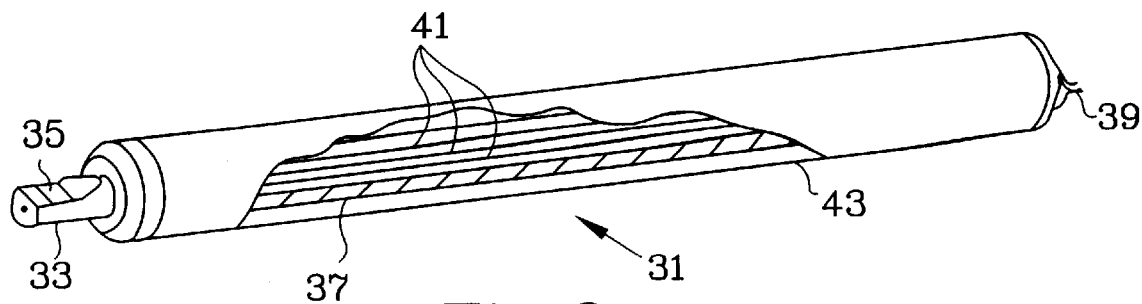
FIG. 2 is a partial cut-away perspective view of the sensor probe according to the present invention.

Referring to FIG. 2, a sensor apparatus, taught here in the context of a pH sensor probe 31, has a ISFET housing 33 containing a media through-hole 35 therein. The housing 33 is composed of any thermoplastic engineering grade plastic suitable for the intended sensing environment. Extending from the ISFET housing 33 is a printed circuit board 37 ending at its distal end in electrical conductors 39. The printed circuit board 37 makes electrical connection between electrical conductors 39 and the ISFET (not shown) through printed wiring runs 41 located on a first side of PCB 37. The ISFET housing 33 and PCB 37 extend through the length of the pH sensor probe 31 to join with the outer body 43. The outer body 43 is made of a material selected to withstand the type of media environment to which the probe is to be exposed.

Figure 3A:
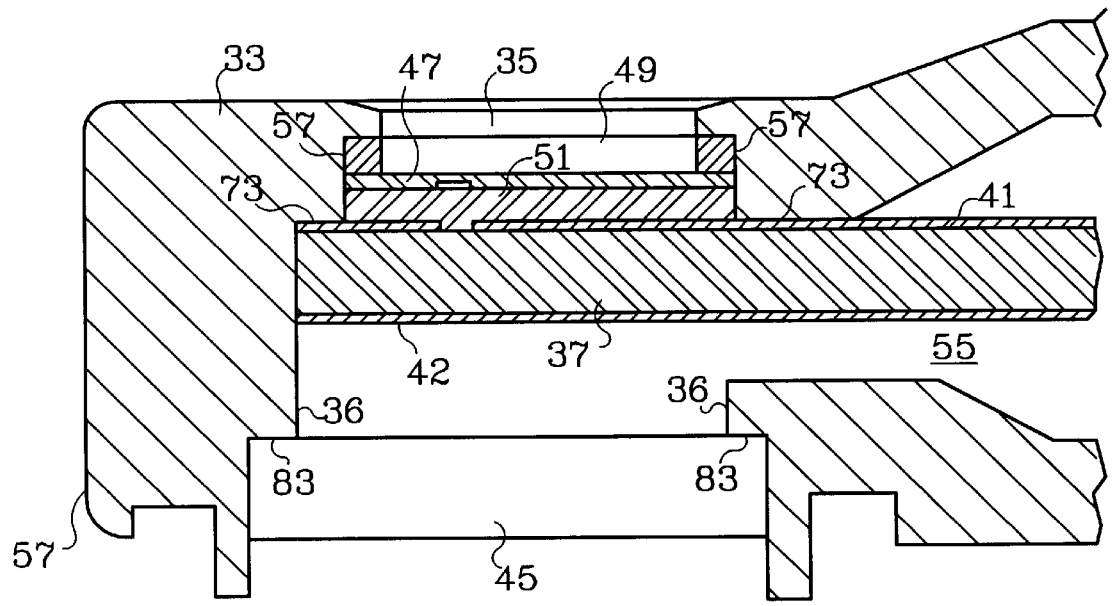
FIG. 3 is a cross-sectional view of a partially completed sensor probe according to the present invention.
Figure 3B:
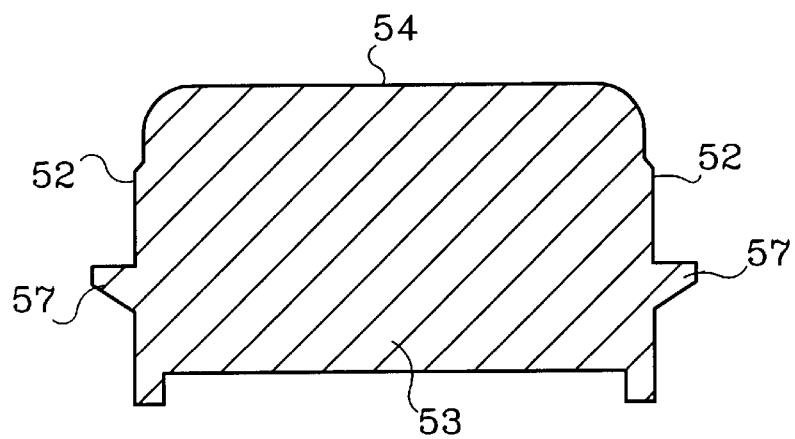

As seen in the schematic cross section views of FIG. 3 and FIG. 5, the microelectronic ISFET housing 33 is a substantially cylindrical-shaped housing with the media through-hole 35 on a first side thereof and an opposing through-hole 45 of a substantially larger size to permit placement therethrough of the microelectronic die of the ISFET 47, the media seal 49 and conductive seal 51 as further explained below. The PCB 37 is further contained within the ISFET housing 33, as is plug member 53. The plug member 53 is shown in an intermediate or in-work position prior to completion of the assembled and sealed ISFET housing.

Figure 1B:
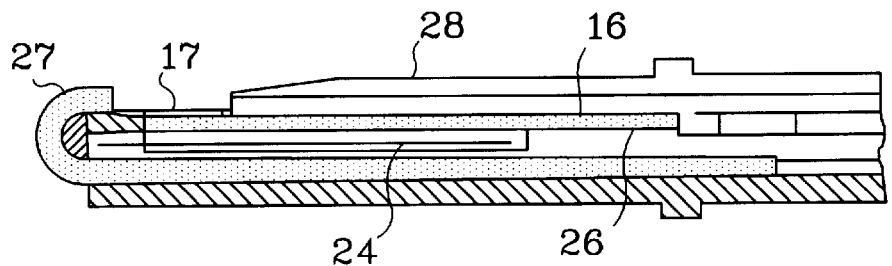

Plug member 53 is composed, in this preferred embodiment, of a 20% to 40% graphite-filled, engineering-grade thermoplastic or plastic material, to be electrically conductive, and forms thereof a pH insensitive electrode or counter electrode of the pH sensor probe 31. The conductive plug member 53 makes electrical contact at surface 54 with printed wiring runs 42, located on a second side of the PCB 37. An electrical field is thus generated at the conductive plug member 53, thereby forming a counter electrode that eliminates the need for the separate "J"-shaped Hastelloy counter electrode 27 shown exiting the body at FIG. 1B and a counter electrode that has a substantially similar thermal expansion coefficient as the ISFET housing 33. As can be appreciated by those skilled in the art, the conductive plug member 53 forms an integral, one-piece, electrode plug member that: i) serves to provide a counter electrode that is in close proximity to the ISFET sensor, providing therefor the best possible position to capture spurious AC and DC currents before they affect the ISFET; and ii) serves to mechanically lock and seal the principal components of the pH sensor probe 31 within ISFET housing 33.

The central bore 55 of the ISFET housing 33 is enlarged at the proximal end 57 to provide a nesting cavity 59 for containment of the ISFET 47 and elastomeric seals 49 and 51. The cavity 59 communicates with the media hole 35. The back hole 45 opposite the media hole 35 also communicates with the central bore 55, allowing the electrode plug member 53 to contact the PCB 37, forcing it into contact with the conductive seal 51 when the electrode plug member 53 is press fit in locking engagement with ISFET housing 33.

Figure 4:
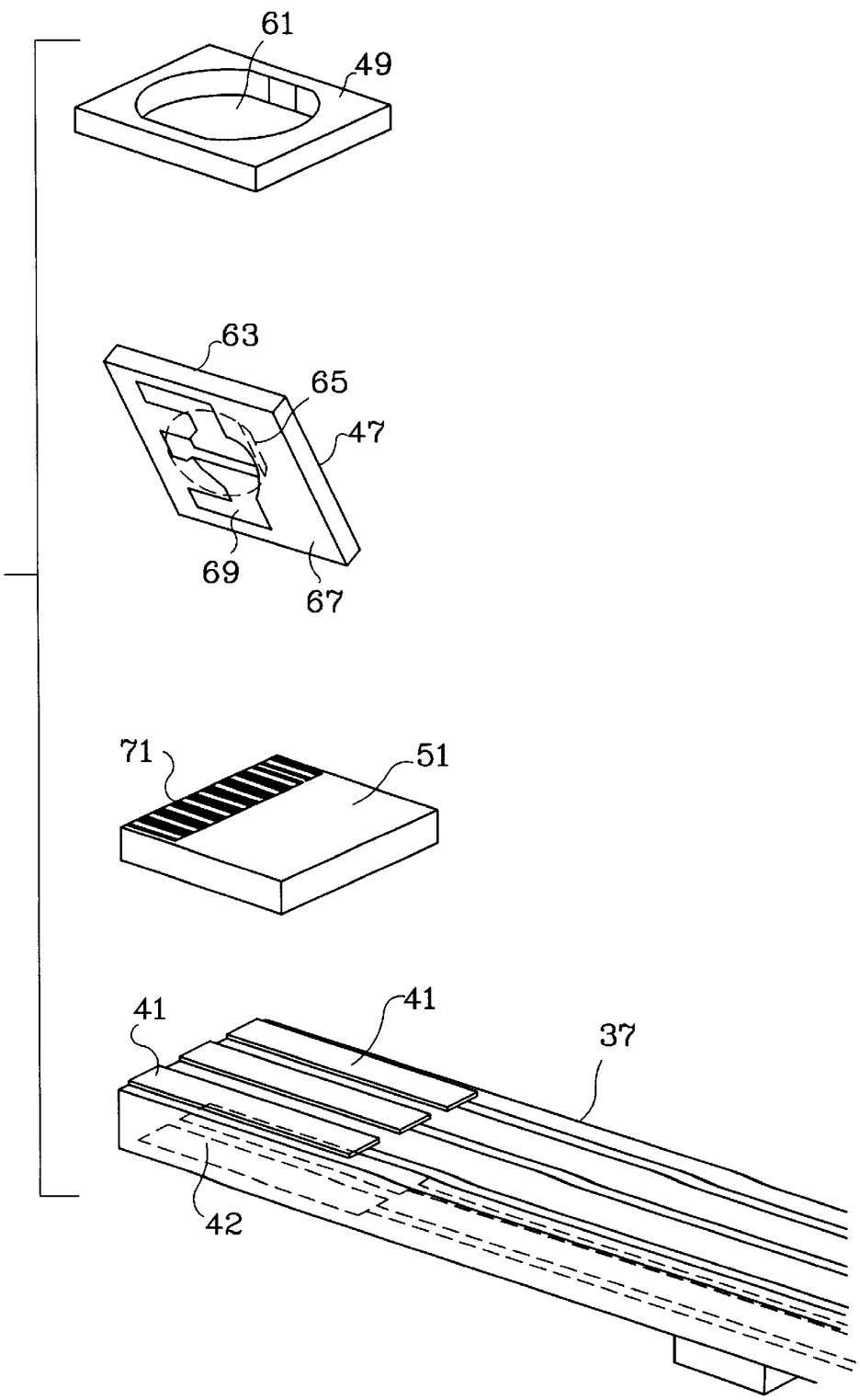
FIG. 4 is an exploded view of the media seal, microelectronic structure, conductive seal, and PCB of the present invention.

Referencing FIG. 4, the principal internal components of the pH sensor probe 31: media seal 49, ISFET die 47, conductive seal 51 and PCB 37 with its printed wiring runs 41 and 42 are shown, from top to bottom, in the order of their placement inside ISFET housing 33 (not shown). The media seal 49 is sized to have its side walls fit in abutting contact with the walls of the nesting cavity 59. The media seal 49 has a central through-hole 61 for alignment with the media hole 35. The media seal is composed of an elastomeric material, impervious to the media into which the sensor is designed to be immersed. It is understood that media seal hardness and compression is selected to provide an effective seal for intended use in the chemical environment over a broad range of temperatures and pressures. For example, ethylene propylene diene monomer (EDPM) of 50–60 durometer with 10% to 35% compression is used in the presently contemplated best mode. It should be noted, that even though an elastomeric material is used herein to compose the media seal, it will be well understood by those skilled in the art that other materials and techniques can be substituted such as gaskets, sealing compounds or the like, that are conformable so as to provide a hermetic seal between the sensor apparatus electronics and the media environment.

The ISFET die 47 is designed to abut the media seal 49 on a first side 63 thereof, which contains the ISFET sensing area 65 conditioned to be ion sensitive to the media to be sensed. A second side 67 of the die contains patterned electrical leads 69 as necessary for the operation of the ISFET. Abutting the second side 67 of the die 47 is an elastomeric conductive seal 51 commercially known as a "silver stacks connector" with conductive silver strips 71 placed therein to allow electrical conduction in the Z axis, i.e., through the thickness of the conductive seal, thereby providing electrical connection between the die 47 and the printed wiring runs 41 of the PCB 37 when the components are loaded in opposition to each other within the ISFET housing (not shown).

Figure 8A:
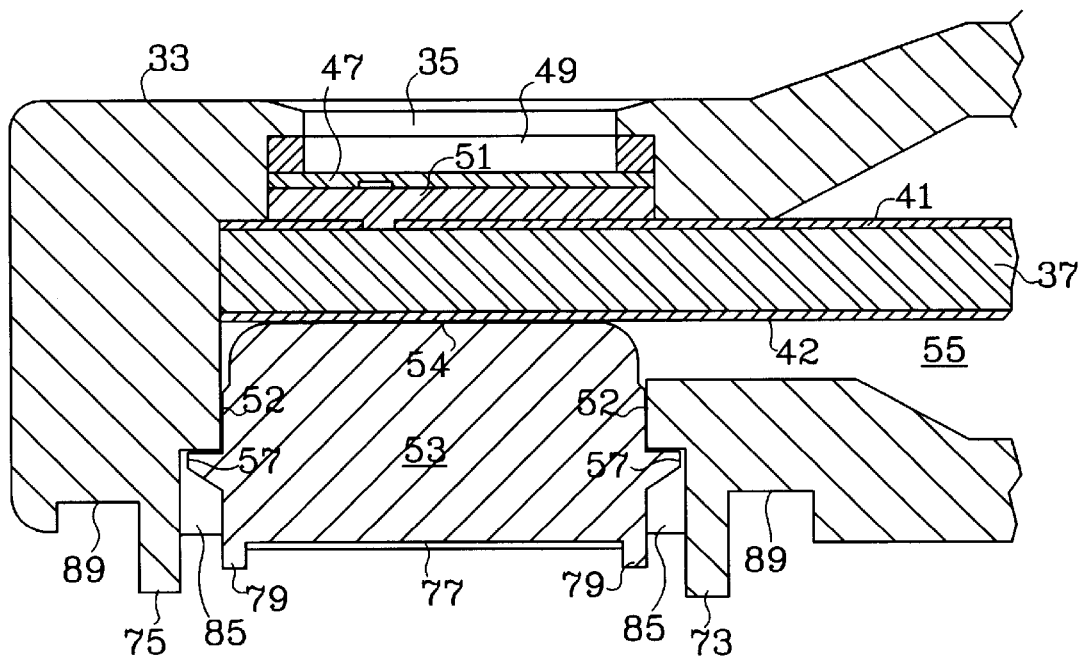
FIG. 8A is a cross-sectional view of a completed sensor probe according to the present invention.

Referring again to FIGS. 3 and 4, it can be seen that the media seal 49 is placed in the nesting cavity 59 which communicates with the media hole 35, with a major plane face of the seal substantially parallel to the long axis of the central bore 55. The ISFET 47 is then placed in the nesting cavity 59 in contact with media seal 49 so that its ion sensing area 65 is aligned with the media seal through-hole 61, placing the patterned electrical lead 69 of the second ISFET surface 67 towards the central bore 55. Elastomeric conductive seal 51 is then placed in the nesting cavity 59 so that its silver conductive strips 71 contact the patterned electrical leads 69 of the ISFET 47. The elastomeric conductive seal 51 in its unloaded state rests slightly above the collar 73 of cavity 59 in its unloaded state. The PCB 37 is then inserted through the central bore of the ISFET housing 33 above the conductive seal 51. The PCB 37 is then tipped down to preload the seals 51 and 49 and the die 47 therebetween to the predetermined depth and/or compression of the collar 73. While the PCB is in this position, the electrode plug member 53 is inserted through back hole 45 and is mechanically engaged in a press-fit manner to the ISFET housing 33 while pressing the PCB 37 in loading contact with the conductive seal 51. The electrode plug member 53 includes extended shoulder areas 52 that engage in a frictional fit against interior surfaces 36 of ISFET housing 33. The electrode plug member 53 is inserted into back hole 45 until landing projections 57 rest on surfaces 48. As can be seen in FIG. 8A, when fully seated within back hole 45, electrode plug member 53 provides a substantially flush outer wall that seals the ISFET body 33 in the area of back hole 45 and forms a hermetic seal between ISFET housing 33 and the ISFET die 47 via the media seal 49. It has been found that a compression force of approximately 10% to 35% is sufficient to seal the ISFET die 47 against the housing 33, thereby preventing the media environment from entering into the interior of ISFET housing 33 and the internal components of the pH sensor probe. Flush mounting of the electrode plug member is preferred where the probe is to be immersed in a flowing liquid, but is not considered a necessity for mating the plug member and housing outside surface in all embodiments of the present invention. All internal electrical components are locked in place with the elastomeric seals providing the necessary cushioning for the ISFET to prevent breakage thereof during mechanical operations.

Figure 7:
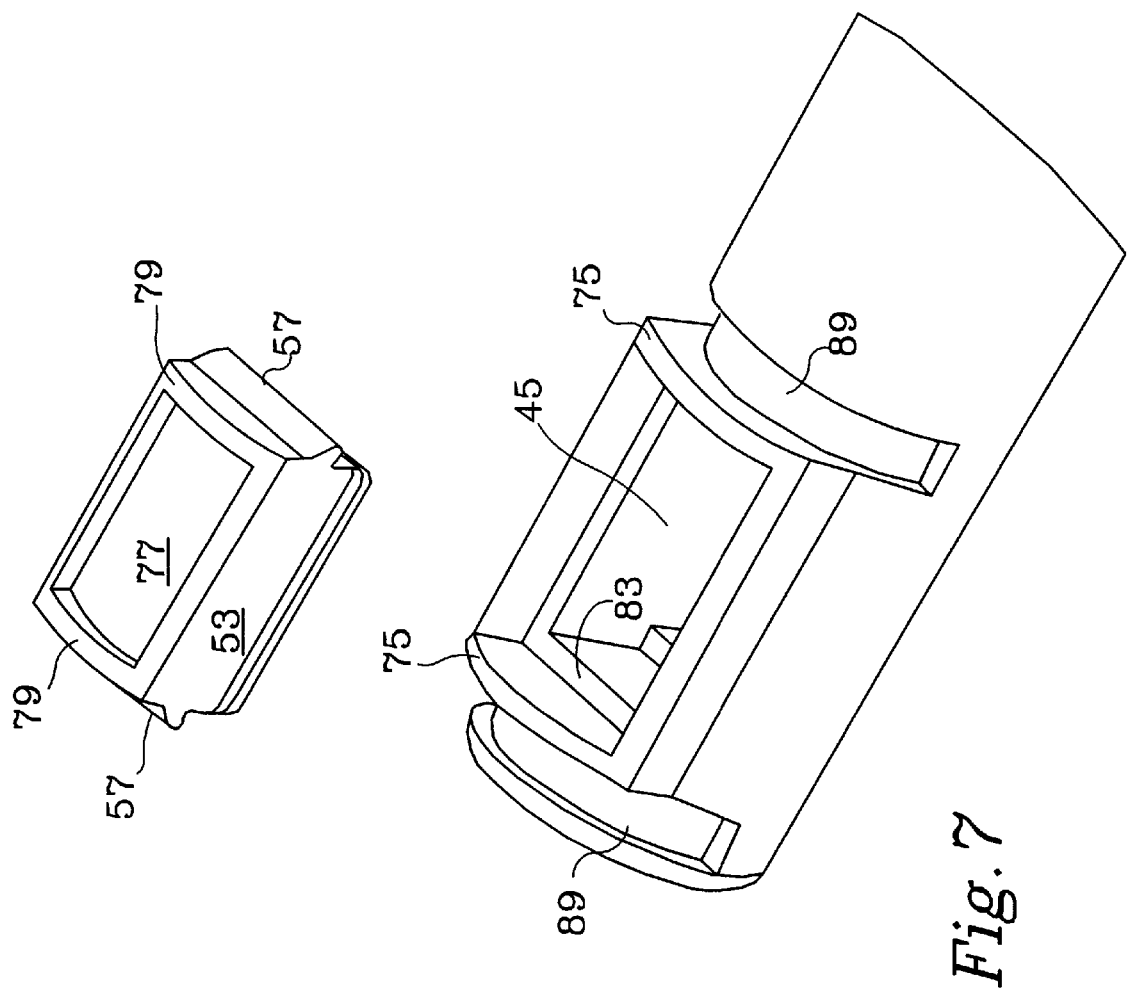

The present invention further includes means for hermetically sealing the electrode plug member 53 from the media environment when the sensor is contemplated to be used in a high-temperature and—pressure operating environment. Referencing FIGS. 5, 6 and 7, it can be seen that the ISFET housing back hole 45 has a integral circumferential collar 75 extending outwardly from the outer edge of a shoulder 83, extending between the back hole 45 and the collar 75. The back hole 45 and its area leading to the central bore 55 are shaped to accept and secure in a press-fit manner the electrode plug member 53 (FIG. 6). The electrode plug member 53 is radiused at its outside surface 77 to be substantially similar to the radius of the outside wall of ISFET housing 33, which is of a substantially cylindrical shape. Extending from the outside surface 77 of the electrode plug member 53 is an integral circumferential collar 79.

Figure 8B:
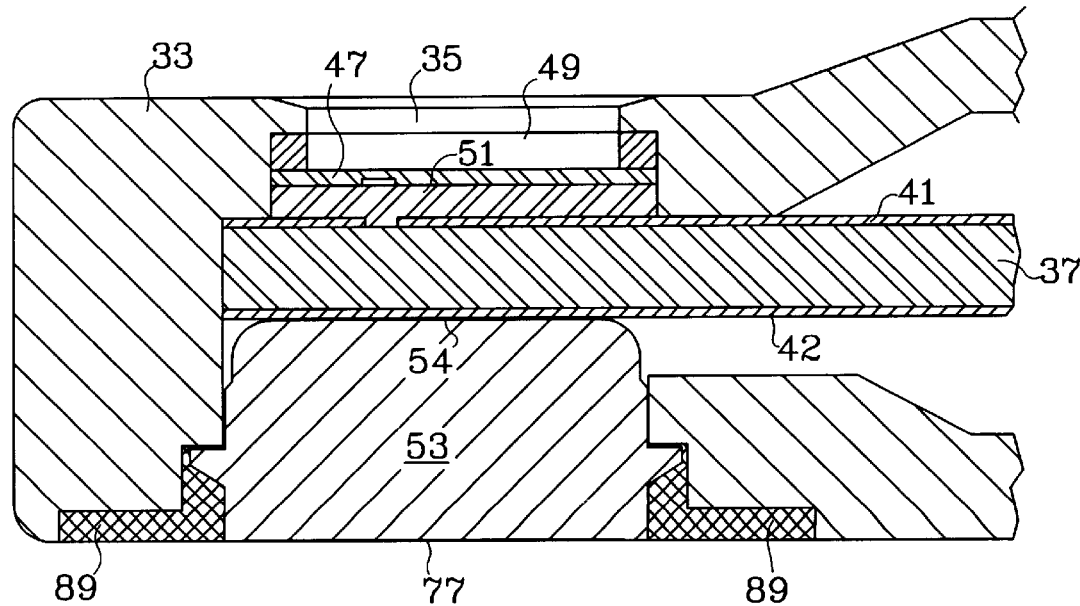
FIG. 8B is a cross-sectional view of the completed sensor probe of FIG. 8A after hermetically sealing the plug member.

Once the electrode plug member 53 is press fit into ISFET housing back hole 45, the circumferential collar extensions of each member are aligned with a space therebetween comprising a well 85 between the collar extensions 75, 79 whose bottom is the shoulder 83. A heat seal anvil 87 of the proper radius to serve as a molding element for the desired final shape, in this case flush and cylindrical, is then brought down to melt the housing and plug collar members together. As can be seen in FIG. 8B, the collar material then melts and flows into the well 85, whereupon the anvil 87 is brought to below melt temperature to set the plastic and then removed, thereby providing a substantially flush outer wall with a hermetic seal in the back hole area of the ISFET housing 33. In the preferred embodiment, the plug collar 79 is designed to melt away from the electrode plug member 53 and blend with the body material to ensure that conductive thermoplastic material remains at the surface 77. Relief areas 89 are further provided in the housing body as a catch basin for collar melt material to maintain a flush housing body outer wall (FIG. 8B). It will be well understood by those skilled in the art that the heat sealing method just described is one of many methods that can be used to provide a hermetic seal of conductive plug member 53 to ISFET housing 33, such as employing material fusion techniques using lasers, ultrasonics, radiant heat or the like. Additionally, hermetic sealing may also be accomplished by the application of a liquid or semi-liquid sealing compound within relief areas 89 to effectively form a hermetic seal and, therefore, the invention is not limited thereto.

The present invention has been described with particular reference to the preferred embodiments thereof. It will be obvious that various changes and modifications can be made therein without departing from the spirit and scope of the invention as defined in the appended claims.

What is claimed is:

1. An ion-sensitive probe comprising:
   a. a housing having a central bore and a first end open to the central bore, a back hole and a media hole in the housing in fluid communication with the central bore, and a cavity communicating with the media hole;
   b. an elastomeric media seal, having a through-hole therein in fluid communication with the media hole and sized to fit within the cavity for hermetically sealing the fluid passage through the media hole to the central bore except by way of the through-hole;
   c. an ion-sensitive semiconductor within the cavity having a first side with a sensing area and a second opposing side with patterned electrical leads in electrical communication with the sensing area, the sensing area in fluid communication within the media seal through-hole;
   d. a PCB, with electrical leads on first and second surfaces thereof, extending through the first housing opening and the central bore, at least some of the PCB electrical leads on the first surface of the PCB contacting the ion sensitive semiconductor; and
   e. an electrically conductive plug constructed to be inserted into the back hole and arranged to have at least some of the PCB electrical leads on the second surface of the PCB contacting the plug, whereby the plug is mechanically engaged in the back hole so as to press the media seal into a hermetically-sealed position against the housing.

2. The ion sensitive probe according to claim 1, further comprising:
   an elastomeric conductive seal within the cavity having patterned conductors extending from a first side thereon to a second side, the conductive seal conductors of the first side being in electrical communication with the patterned electrical leads of the ion sensitive semiconductor.

3. The ion-sensitive probe according to claim 1, wherein the plug is constructed of an electrically conductive material and functions as a counter electrode.

4. The ion-sensitive probe according to claim 3, further comprising:
   means for hermetically sealing the plug to the housing.

5. The ion-sensitive probe according to claim 1, further comprising:
   a means for sealing the central bore first end.

6. A sensor package comprising:
   a. a thermoplastic housing having a cavity including a media hole, a back hole and a fluid passage;
   b. an ion-sensitive sensor arranged to be admitted through the back hole into the cavity;
   c. electrical connection means extending through the cavity for electrically connecting the sensor;
   d. an electrode arranged to be admitted into the back hole to connect to the electrical connection means and to load the sensor in communication with the fluid passage and the electrical connection means; and
   e. the housing being constructed to hermetically seal the sensor to the housing when the ion-insensitive electrode is fully inserted into and mechanically engaged in the back hole.

7. The sensor package according to claim 4, further comprising:
   resilient means for cushioning the sensor from the loading force of the ion-insensitive electrode.

8. The sensor package according to claim 4 wherein, the package further comprises:
   sealing means for creating the hermetic seal between the sensor and the housing when the ion insensitive electrode is mechanically engaged in the back hole.

9. The sensor package according to claim 4, wherein the ion-insensitive electrode is constructed of an electrically conductive plastic material.

10. The sensor package according to claim 9 wherein, the package further comprises:
    means for hermetically sealing the ion-insensitive electrode to the housing after the electrode is mechanically engaged in the back hole.

11. An ion-sensitive probe comprising:
    a. a housing having a central bore, a back hole and a media hole in fluid communication with the central bore;
    b. a media seal, having a through-hole therein in communication with the media hole, for hermetically sealing the fluid passage through the media hole to the central bore except by way of the through-hole;
    c. an ion-sensitive electrode having a first side with a sensing area and a second opposing side with patterned electrical leads in electrical communication with the sensing area, the sensing area in fluid communication within the media seal through-hole;
    d. an elastomeric conductive seal having patterned conductors extending from a first side thereon to a second side, the conductive seal conductors of the first side being in electrical communication with the patterned electrical leads of the ion sensitive electrode;
    e. a PCB, with electrical leads on first and second surfaces thereof, extending through the first housing opening and the central bore, at least some of the PCB electrical leads on the first surface of the PCB contacting the patterned conductors of the elastomeric conductive seal second side; and
    f. an ion-insensitive plug constructed and arranged to be inserted into the back hole arranged to contact the PCB electrical leads on the second surface of the PCB, whereby the ion insensitive plug is mechanically engaged in the back hole so as to press the media seal into a hermetically sealed position against the housing.

* * * * *

UNITED STATES PATENT AND TRADEMARK OFFICE
CERTIFICATE OF CORRECTION

PATENT NO: 6,117,292

DATED: September 12, 2000

INVENTOR(S): Farid Ahmad

It is certified that an error appears in the above-identified patent and that said Letters Patent are hereby corrected as shown below:

In the Inventor: Add James G. Connery, Maple Glen, PA

-- James G. Connery, Maple Glen, PA --

Signed and Sealed this

Twenty-fourth Day of April, 2001

Attest:

NICHOLAS P. GODICI

*Attesting Officer*   *Acting Director of the United States Patent and Trademark Office*